United States Patent [19]

Yasuda et al.

[11] 4,346,585
[45] Aug. 31, 1982

[54] GAS DETECTOR

[75] Inventors: Eturo Yasuda; Yoshihiro Segawa, both of Okazaki; Minoru Ohta, Anjo, all of Japan

[73] Assignee: Nippon Soken, Inc., Nishio, Japan

[21] Appl. No.: 213,104

[22] Filed: Dec. 4, 1980

Related U.S. Application Data

[62] Division of Ser. No. 958,681, Nov. 8, 1978, Pat. No. 4,287,751.

[30] Foreign Application Priority Data

Nov. 9, 1977 [JP] Japan .................................. 52/134259

[51] Int. Cl.³ ............................................. G01N 27/04
[52] U.S. Cl. ........................................... 73/23; 338/34
[58] Field of Search ................... 73/23, 27 R; 338/34; 422/98

[56] References Cited

U.S. PATENT DOCUMENTS 3,886,785  6/1975  Stadler et al. .......................... 73/23
4,187,486  2/1980  Takahashi et al. .................... 338/34

Primary Examiner—Stephen A. Kreitman
Attorney, Agent, or Firm—Cushman, Darby & Cushman

[57] ABSTRACT

A gas detector used with an automobile exhaust gas purifier system is disclosed, in which that part of the gas detector element of a sintered metal oxide which is located between electrodes for picking up a detected output has the thickness of 0.1 mm to 0.6 mm.

4 Claims, 6 Drawing Figures

GAS DETECTOR

This is a division of application Ser. No. 958,681, filed Nov. 8, 1978, now U.S. Pat. No. 4,287,751.

BACKGROUND OF THE INVENTION

1. Field of the Invention

This invention relates to a gas detector used with an exhaust gas purifier system of feedback type employing, for example, a three-way catalyst.

2. Description of the Prior Art

In order to reduce or eliminate the obnoxious components contained in the automobile exhaust gas, the ratio between the air taken into the engine and the fuel, i.e., what is called the air-fuel ratio is required to be regulated accurately. Especially, if the obnoxious components are to be reduced simultaneously by the use of a three-way catalyst, the air-fuel ratio is required to be regulated in a range very near to the stoichiometric air-fuel ratio. For this purpose, a detector is necessary which makes possible accurate regulation of the air-fuel ratio on the one hand and is durable on the other hand. The conventional well-known detector includes an oxygen concentration detector element made of such a material as zirconium oxide, or a gas detector element using a metal oxide for indicating changes in electric resistance dependent on the oxygen pressure component.

As compared with the oxygen concentration detector element for detecting the changes in electromotive force which acts as an oxygen concentration cell using a solid electrolyte such as zirconium oxide, the gas detector element using a metal oxide, especially, a sintered oxide of a transition metal has the advantage that electrodes are easily mounted onto the gas detector element and the versatility in the shaping thereof enables easy manufacture with a lower cost. The conventional gas detector elements, however, have a considerably longer response time to the changes in concentration of the gas components than the oxygen concentration detector element.

The response time is the sum of the time required for fresh gas to penetrate the inner part of the detector element by replacing the old gas therein, and the time before such a gas is absorbed by particles of the metal oxide or by mutual coupling portions of such particles making up the gas detector element present intermediately of a pair of pick-up electrodes in spaced relation and oxidation or reduction of the metal oxide particles is caused to increase or decrease the amount of free electrons. In the case of a gas detector element made of an oxide of an n-type semiconductor metal of $TiO_2$, for instance, the electric resistance of the oxide is low in a reduction atmosphere where the air-fuel ratio is higher than the stoichiometric air-fuel ratio and high in an oxidation atmosphere where the air-fuel ratio is lower than the stoichiometric air-fuel ratio. Comparison between the response time when the air-fuel ratio is transferred from the higher to lower value and the response time when the air-fuel ratio is transferred from the lower to higher value shows that the response time is shorter when the air-fuel ratio is transferred from the lower to higher value. This is for the reason that when the air-fuel ratio is transferred from the lower to the higher side, the high electric resistance of the surface portion of the oxide which results on the lower side of air-fuel ratio decreases by contacting the gas of lower air-fuel ratio to cause a sudden change in the entire resistance, while when the air-fuel ratio is transferred from the higher to lower side, the entire resistance does not suddenly change until the gas penetrates inner part of the gas detector element to change the low resistance on the lower side to higher resistance. For this reason, it is important to shorten the time required for the gas to penetrate the inner part of the gas detector element.

SUMMARY OF THE INVENTION

Accordingly, it is an object of the present invention to provide a gas detector in which the gas penetration distance is shortened thereby to lessen the gas penetration time and in order to shorten the distance of penetration of the detected gas into the part of the gas detector element between a pair of electrodes, the thickness of the part of the gas detector element associated with the gas penetration distance between the pair of electrodes is made 0.1 to 0.6 mm.

DETAILED DESCRIPTION OF THE PREFERRED EMBODIMENTS

Figure 1:
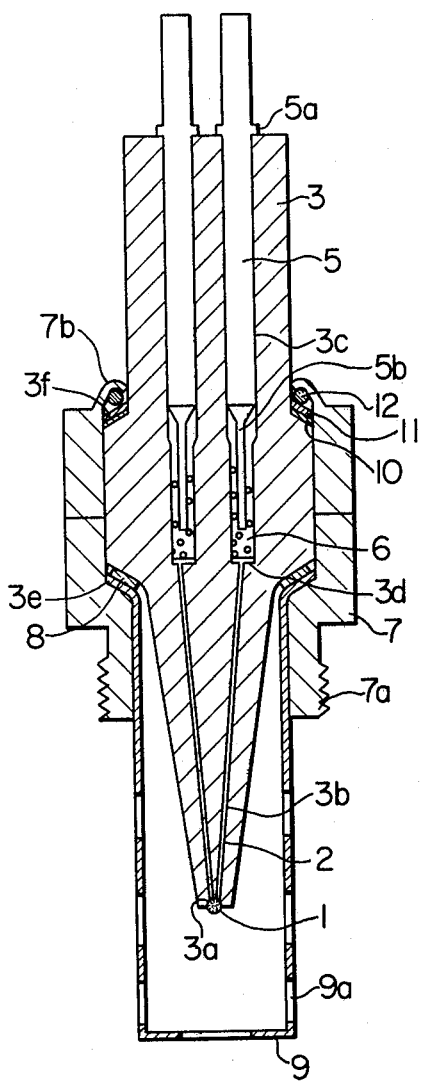
FIG. 1 is a sectional view showing a general construction of an embodiment of the gas detector according to the present invention.
Figure 2:
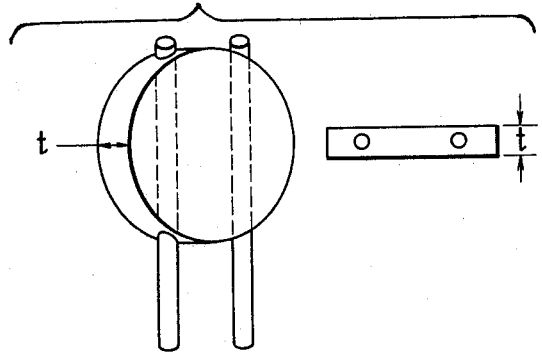
FIG. 2 is a perspective view showing the gas detector element shown in FIG. 1.

The embodiments of the invention shown in the drawings will be explained below. In FIGS. 1 and 2, reference numeral 1 shows a gas detector element in the shape of a thin disc having the diameter of 2 mm and the thickness (t) of 0.28 mm. The gas detector element 1 is constructed of a sintered $TiO_2$ exhibiting the electric resistance corresponding to the detected gas component. The gas detector element 1 is embedded with ends of a pair of Pt electrodes 2 having the diameter of 0.2 mm and spaced from each other. The pair of electrodes 2 is for measuring the electric resistance value offered by the gas detector element 1. Numeral 3 shows a holding member made of a heat-resistant metal oxide such as alumina of high electric insulation. The end of the holding member 3 where the element 1 is to be mounted is formed with a spherical recess 3a in which about one third of the gas detector element 1 is received for preventing the gas detector element 1 from falling in the exhaust gas. The pair of electrodes 2 embedded in the gas detector element 1 are inserted into the through holes 3b formed axially of the holding member 3. The lead wires 5 of conductive metal having the flanges 5a and the knurled parts 5b are inserted into the through holes 3c provided in the holding member 3. The electrodes 2 are electrically connected to the lead wires 5 by conductive glass 6 such as copper glass. The bottom part of the through hole 3c where the electrodes 2 are connected with the lead wires 5 by means of the conductive glass 6 has a square flat part 3d to which, as shown in the drawing, the end of the electrode 2 is secured by being bent, thus preventing the gas detector element 1 from floating up or separating. In order to form the square flat part 3d, the through hole 3c is narrowed midway, thus facilitating the separation of a mold from the surrounding wall of the hole 3c in the case of molding the holding member. Numeral 7 shows a housing of heat-resistant metal having a threaded portion 7a for mounting an exhaust tube or like. The washer 8 of heat resistant metal and a protective cover 9 of heat-resistant metal with holes 9a allowing the passage of exhaust gas are mounted around tapered lower part 3e of the holding member 3. Around tapered upper part 3f thereof, on the other hand, asbestos 10, washer 11 and ring 12 of comparatively soft metal such as copper are secured. The upper part 7b of the housing is caulked, thus securing the holding member 3 and the housing 7 to each other.

An example of the method for fabricating the gas detector element 1 will be explained below. Rutile $TiO_2$ calcined at 1200° C. is crushed in a ball mill into comparatively fine and uniform particles with diameters of 0.1 to 10μ or preferably 0.1 to 3μ on the average. This is mixed with an organic binder solution comprised of an organic solvent, a binder and a plasticizer in the kneader, thus forming a slurry. Next, by use of "doctor blade method", two sheets each about 0.1 mm thick are prepared, between which the electrodes are inserted. The resulting assembly is integrally compressed, molded, and calcined thus producing the gas detector element 1.

Figure 3:
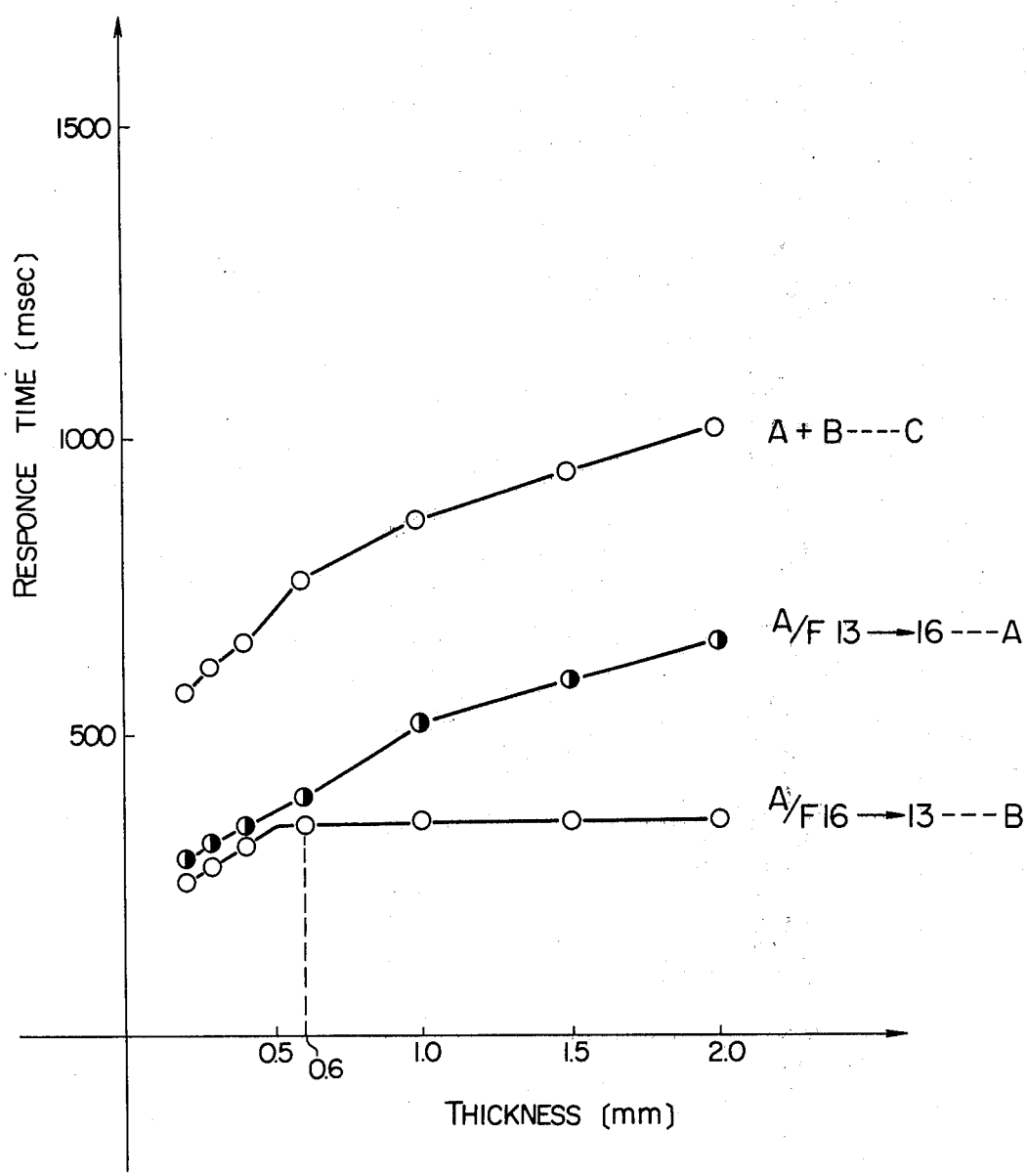
FIG. 3 is a characteristics diagram showing the relation between the thickness and response time of the gas detector element for explaining the effect of the present invention.

Next, the relation between the response time and the thickness t of the gas detector element between the two electrodes 2 was studied (See FIG. 2), and the result thereof is shown in FIG. 3. In FIG. 3, with the gas detector element 1 placed within the exhaust gas of 500° C. emitted from the internal combustion engine of the automobile, the line A represents the time required for the low resistance under the condition of A/F equal to 13 to change to the high resistance under the condition of A/F equal to 16, when the air-fuel ratio A/F is changed from the ratio 13 to 16. Further, the line B shows the time required for the high resistance resulting under the condition of the air-fuel ratio 16 to the low resistance resulting under the condition of the air-fuel ratio 13 when a change-over is made from A/F 16 to A/F 13. Furthermore, the line C shows the sum of the times represented by the lines A and B. As obvious from FIG. 3, the response time is shorter, the smaller the thickness of the gas detector element 1 between the electrodes 2. When the thickness exceeds 0.6 mm, the response time suddenly becomes long when the air-fuel ratio 13 is changed to 16 as shown by line A. When A/F is changed from 16 to 13, on the other hand, as shown in line B, the response time remains substantially the same even when the thickness exceeds 0.6 mm. By the way, if the gas detector element 1 is too thin, the strength thereof is reduced and such a thin element may give rise to insufficient contact with the electrodes 2 which may in turn cause unstable holding of the electrodes 2, and therefore the thickness of the gas detector element 1 between the electrodes 2 is preferably not less than 0.1 mm. The inventors have found that if the thickness of the gas detector element 1 between the electrodes 2 is from 0.1 to 0.6 mm, the catalyst such as Pt is capable of being sufficiently carried up to inner portion of the gas detector element 1.

Figure 4:
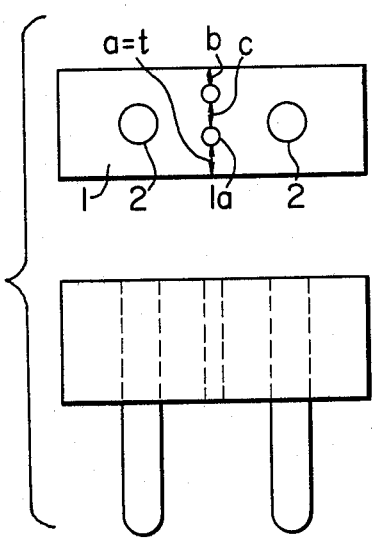
FIG. 4 is a sectional view of the gas detector element according to another embodiment of the present invention.

The diagram of FIG. 4 shows a cross sectional view of the disc-shaped gas detector element according to another embodiment in which two through-holes 1a are formed between the pair of the electrodes 2. The detected gas freely enters or flows out the through holes 1a of this embodiment. If the relation a>b>c is satisfied among the sizes of a, b and c in the drawing, the size a is the desired thickness t of the gas detector element 1 between the electrodes 2. In the embodiment under consideration, the diameters of the two holes 1a and the lengthes of b and c are added to the length a=t, and therefore the whole thickness is enlarged, thereby simplifying the work for embedding the electrodes 2. The two holes 1a may be replaced by one hole or three or more holes in so far as the thicker one of the remaining electrode material portions is determined as the length t. A wider element contributes also to a higher mechanical strength of the device as a whole. Assume, for example, the case in which the air-fuel ratio is changed from the rich value to lean value. The parts b and c are oxidated to achieve their high resistance earlier than the remaining ports. However, the widest part a is more slowly penetrated by the gas than the other parts, and oxidation is slowly effected therein ($TiO_2$ is an insulating material). Therefore, the resistance changing response characteristic is such as shown in FIG. 3 determined by the part a, the thickness of which may be preferably selected as t.

Incidentally, the through holes 1a are formed in such a manner that metal wires are sandwiched between the above-mentioned sheets, and after being compressed and molded, extruded, and the resulting assembly is calcined. In place of the metal wires, a combustible material such as polyurethane may be inserted and calcined to form such through holes.

Figure 5:
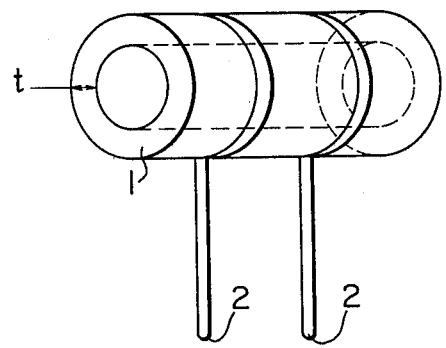
FIG. 5 is a perspective view showing the gas detector element according to another embodiment of the present invention.

FIG. 5 shows another embodiment in which the gas detector element 1 is hollow and fixedly wound with the electrodes 2, in which case the thickness of the element 1 between the pair of electrodes refers to the length t in the Figure.

Figure 6:
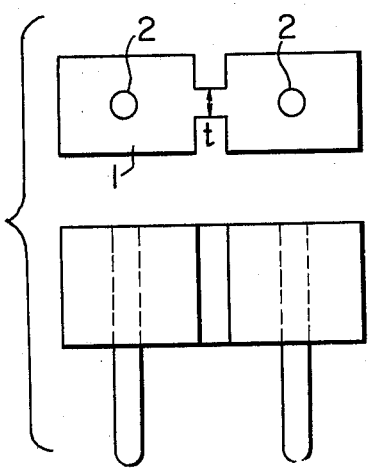
FIG. 6 is a sectional view showing the gas detector element according to still another embodiment of the present invention.

The diagram of FIG. 6 illustrates still another embodiment of the invention in which that part of the gas detector element 1 in the form of rectangular parallelopiped which is associated with the gas penetration distance between the pair of electrodes 2 is partially thinned to the thickness of t. By the configuration as shown in FIG. 5 or 6, the size of the whole device can be increased, thus facilitating the mounting of the electrodes and the fabrication of the element itself. This is for the reason that although the part with the thickness of t is left between the electrodes, the thickness and size of the whole device is enlarged as compared with the case where the whole structure has the thickness of t. The sintered material making up the gas detector element 1 may be ZnO, NiO or SnO instead of $TiO_2$.

It will be understood from the foregoing description that according to the present invention, the thickness of that part of the gas detector element between a pair of spaced electrodes which is associated with the gas penetration distance is made 0.1 to 0.6 mm, and therefore the variation in the value of electric resistance, i.e., the response of the gas detector element 1 in response to changes in the concentration of the gas component to be detected is quicker. At the same time, the difference is lessened between the response time required for the change in electric resistance in transfer from high to low concentration of gas component and the response time required for the reverse change in electric resistance in transfer from the low to high concentration. As a result, the difference between the actually-detected concentration of the gas component and that set beforehand can be reduced, thus increasing the control accuracy.

We claim:

1. A gas detector comprising: a pair of electrodes; and a gas detector element comprising a sintered metal oxide block having two parallel opposed rectangular surfaces, said block having an electrical resistance that is a function of a gas to be detected, said electrodes being parallel to one another, normal to a lengthwise axis thereof, lying in a plane disposed centrally between and parallel to said surfaces, spaced a first predetermined distance apart, and embedded in and extending substantially through said block from one side to an opposing side to define a portion thereof, said portion having at least one notch disposed at said surface and extending therethrough, forming a further portion therebetween, said further protion extending substantially therethrough and of a predetermined thickness less than 0.6 millimeters for shortening the penetration time therethrough of said gas.

2. The gas detector of claim 1, wherein a pair of uniform opposing notches are formed on said surfaces.

3. The gas detector of claim 2, wherein said notches are parallel to and substantially equidistant from said electrodes.

4. The gas detector of claim 1, 2, or 3, wherein said predetermined thickness is greater than about 0.1 millimeters.

* * * * *